US012668823B2

(12) United States Patent
Shin et al.

(10) Patent No.: US 12,668,823 B2
(45) **Date of Patent: *Jun. 30, 2026**

(54) MICROORGANISM HAVING INCREASED ACTIVITY OF 3-METHYL-2-OXOBUTANOATE HYDROXYMETHYLTRANSFERASE, AND USE THEREOF

(71) Applicant: CJ CheilJedang Corporation, Seoul (KR)

(72) Inventors: Kwang Soo Shin, Seoul (KR); Kwang Woo Lee, Seoul (KR); Yee-Seul So, Seoul (KR); Yeon-Jae Jang, Seoul (KR); Jihyun Shim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 356 days.

This patent is subject to a terminal disclaimer.

(21) Appl. No.: 17/766,389

(22) PCT Filed: Jul. 1, 2021

(86) PCT No.: PCT/KR2021/008349

§ 371 (c)(1),
(2) Date: Apr. 4, 2022

(87) PCT Pub. No.: WO2022/005225

PCT Pub. Date: Jan. 6, 2022

(65) Prior Publication Data

US 2024/0167065 A1 May 23, 2024

(30) Foreign Application Priority Data

Jul. 1, 2020 (KR) ........................ 10-2020-0081194

(51) Int. Cl.

| | |
|---|---|
| ***C12P 13/02*** | (2006.01) |
| ***C12N 9/10*** | (2006.01) |
| ***C12N 15/77*** | (2006.01) |
| ***C12P 7/42*** | (2006.01) |
| ***C12R 1/15*** | (2006.01) |

(52) U.S. Cl.

CPC ............ *C12P 13/02* (2013.01); *C12N 9/1014* (2013.01); *C12N 15/77* (2013.01); *C12P 7/42* (2013.01); *C12R 2001/15* (2021.05); *C12Y 201/02011* (2013.01)

(58) Field of Classification Search

None

See application file for complete search history.

(56) References Cited

U.S. PATENT DOCUMENTS

| | | | |
|---|---|---|---|
| 5,932,457 A | 8/1999 | Moriya et al. | |
| 6,177,264 B1 | 1/2001 | Eggeling et al. | |
| 7,718,205 B2 | 5/2010 | Eisele | |
| 9,109,242 B2 | 8/2015 | Park et al. | |
| 2003/0073204 A1 | 4/2003 | Rieping | |
| 2024/0167065 A1* | 5/2024 | Shin ....................... | C12N 15/77 |

FOREIGN PATENT DOCUMENTS

| | | |
|---|---|---|
| CN | 1256313 | 6/2000 |
| CN | 105658793 | 6/2016 |
| EP | 0590857 | 11/2003 |
| EP | 2157174 | 2/2010 |
| EP | 2163629 | 3/2017 |
| KR | 1992-0007401 | 8/1992 |
| KR | 10-2000-0047829 | 7/2000 |
| KR | 10-2000-0047833 | 7/2000 |
| KR | 10-2006-0023159 | 3/2006 |
| WO | 97-10340 | 3/1997 |
| WO | 2010-141468 | 12/2010 |
| WO | 2022-239953 | 11/2022 |

OTHER PUBLICATIONS

Accession A0A0E1T219. May 27, 2015 (Year: 2015).*

Bornscheuer et al. Curr Protoc Protein Sci. Nov. 2011;Chapter 26: Unit26.7. (Year: 2011).*

Bo Zhang et al. "Metabolic engineering of *Escherichia coli* for d-pantothenic acid production." Food chemistry 294 (May 8, 2019): 267-275.

Yan-Hui Yang et al. "The functions and biosynthesis of pantothenate." Chemistry of Life 28.4: 448-452, 2008.

Michael E. Webb et al., "Biosynthesis of pantothenate", Natural Product Reports, vol. 21, No. 6, Oct. 28, 2004 (Oct. 28, 2004), p. 695, XP093114692, GB ISSN: 0265-0568, DOI: 10.1039/b316419p.

EPO, Search Report of EP 21833442.3 dated Jun. 2, 2024.

EPO, Office Action of EP 21833442.3 dated Jun. 2, 2024.

KIPO, PCT Search Report & Written Opinion of PCT/KR2021/008349 dated Oct. 12, 2021.

NCBI, GenBank accession No. AFG39014.1, "3-methyl-2-oxobutanoate hydroxymethyltransferase [*Escherichia coli* P12b]", Jan. 31, 2014.

NCBI, GenBank accession No. WP_096976955.1, "3-methyl-2-oxobutanoate hydroxymethyltransferase [*Escherichia coli*]", Jun. 3, 2019.

Carol E. Jones et al., "Cloning and Sequencing of the *Escherichia coli* panB Gene, Which Encodes Ketopantoate Hydroxymethyltransferase, and Overexpression of the Enzyme", Journal of Bacteriology, Apr. 1993, p. 2125-2130.

(Continued)

*Primary Examiner* — Christian L Fronda

(74) *Attorney, Agent, or Firm* — LEX IP MEISTER, PLLC

(57) ABSTRACT

Provided are: a polypeptide having activity of 3-methyl-2-oxobutanoate hydroxymethyltransferase; a microorganism having increased activity of 3-methyl-2-oxobutanoate hydroxymethyltransferase; a composition for producing pantothenic acid and/or pantoic acid, comprising the polypeptide and/or the microorganism, and a pantothenic acid and/or pantoic acid production method comprising a step for culturing the microorganism.

9 Claims, No Drawings

Specification includes a Sequence Listing.

(56) References Cited

OTHER PUBLICATIONS

Samuel Karlin et al., “Applications and statistics for multiple high-scoring segments in molecular sequences”, Pro. Natl. Acad. Sci. USA, 90, 5873, 1993.

William R. Pearson, “[5] Rapid and Sensitive Sequence Comparison with FASTP and FASTA”, Methods Enzymol., 183, 63, 1990.

Sambrook et al., supra,9.50-9.51, 11.7-11.8, Molecular Cloning, A Laboratory Manual, vol. 2, Third Edition.

Satoshi Takeda et al., “Detection of K-ras mutation in sputum by mutant-allele-specific amplification (MASA)”, Hum. Mutation, 2, 112-117 (1993).

Hermann Sahm et al., “D-Pantothenate Synthesis in Corynebacterium glutamicum and Use of panBC and Genes Encoding L-Valine Synthesis for D-Pantothenate Overproduction”, Applied and Environmental Microbiology, vol. 65, No. 5, p. 1973-1979, May 1999.

Christophe Chassagnole et al., “Metabolic network analysis during fed-batch cultivation of Corynebacterium glutamicum for pantothenic acid production: first quantitative data and analysis of by-product formation”, Journal of Biotechnology 104 (2003) 261-272, Sep. 2003.

Brazilian Patent and Trademark Office, Office Action of the corresponding BR Patent Application No. BR1120220087454, dated Jun. 15, 2023.

* cited by examiner

SEQUENCE LISTING

```
<160> NUMBER OF SEQ ID NOS: 73

<210> SEQ ID NO 1
<211> LENGTH: 37
<212> TYPE: DNA
<213> ORGANISM: Artificial Sequence
<220> FEATURE:
<223> OTHER INFORMATION: synthetic_primer

<400> SEQUENCE: 1

tagatcgaaa ggtgcacaaa gatgaaaccg accacca                            37


<210> SEQ ID NO 2
```

-continued

<211> LENGTH: 41
<212> TYPE: DNA
<213> ORGANISM: Artificial Sequence
<220> FEATURE:
<223> OTHER INFORMATION: synthetic_primer

<400> SEQUENCE: 2
ccgctctaga actagtggat cttaatggaa actgtgttct t 41

<210> SEQ ID NO 3
<211> LENGTH: 36
<212> TYPE: DNA
<213> ORGANISM: Artificial Sequence
<220> FEATURE:
<223> OTHER INFORMATION: synthetic_primer

<400> SEQUENCE: 3
tagatcgaaa ggtgcacaaa gatgaaaccg accacc 36

<210> SEQ ID NO 4
<211> LENGTH: 40
<212> TYPE: DNA
<213> ORGANISM: Artificial Sequence
<220> FEATURE:
<223> OTHER INFORMATION: synthetic_primer

<400> SEQUENCE: 4
ccgctctaga actagtggat cttaatggaa actgtgttct 40

<210> SEQ ID NO 5
<211> LENGTH: 38
<212> TYPE: DNA
<213> ORGANISM: Artificial Sequence
<220> FEATURE:
<223> OTHER INFORMATION: synthetic_primer

<400> SEQUENCE: 5
tagatcgaaa ggtgcacaaa gatgaaacca accaccat 38

<210> SEQ ID NO 6
<211> LENGTH: 41
<212> TYPE: DNA
<213> ORGANISM: Artificial Sequence
<220> FEATURE:
<223> OTHER INFORMATION: synthetic_primer

<400> SEQUENCE: 6
ccgctctaga actagtggat cttaatggaa actgtgttct t 41

<210> SEQ ID NO 7
<211> LENGTH: 42
<212> TYPE: DNA
<213> ORGANISM: Artificial Sequence
<220> FEATURE:
<223> OTHER INFORMATION: synthetic_primer

<400> SEQUENCE: 7
tagatcgaaa ggtgcacaaa gatgtcatta aagcaaataa ct 42

<210> SEQ ID NO 8
<211> LENGTH: 41
<212> TYPE: DNA
<213> ORGANISM: Artificial Sequence
<220> FEATURE:
<223> OTHER INFORMATION: synthetic_primer

<400> SEQUENCE: 8
ccgctctaga actagtggat cttattggaa actgtgttct t 41

<210> SEQ ID NO 9
<211> LENGTH: 36
<212> TYPE: DNA
<213> ORGANISM: Artificial Sequence
<220> FEATURE:
<223> OTHER INFORMATION: synthetic_primer

<400> SEQUENCE: 9
tagatcgaaa ggtgcacaaa gatgaaaccc accacc 36

<210> SEQ ID NO 10
<211> LENGTH: 39
<212> TYPE: DNA
<213> ORGANISM: Artificial Sequence
<220> FEATURE:
<223> OTHER INFORMATION: synthetic_primer

<400> SEQUENCE: 10
ccgctctaga actagtggat cttagttaaa tgagtgctc 39

<210> SEQ ID NO 11
<211> LENGTH: 37
<212> TYPE: DNA
<213> ORGANISM: Artificial Sequence
<220> FEATURE:
<223> OTHER INFORMATION: synthetic_primer

<400> SEQUENCE: 11
tagatcgaaa ggtgcacaaa gatgaaaccg accacca 37

<210> SEQ ID NO 12
<211> LENGTH: 40
<212> TYPE: DNA
<213> ORGANISM: Artificial Sequence
<220> FEATURE:
<223> OTHER INFORMATION: synthetic_primer

<400> SEQUENCE: 12
ccgctctaga actagtggat cttaatggaa actgtgttct 40

<210> SEQ ID NO 13
<211> LENGTH: 36
<212> TYPE: DNA
<213> ORGANISM: Artificial Sequence
<220> FEATURE:
<223> OTHER INFORMATION: synthetic_primer

<400> SEQUENCE: 13
tagatcgaaa ggtgcacaaa gatgaaaccc accacg 36

<210> SEQ ID NO 14
<211> LENGTH: 38
<212> TYPE: DNA
<213> ORGANISM: Artificial Sequence
<220> FEATURE:
<223> OTHER INFORMATION: synthetic_primer

<400> SEQUENCE: 14
ccgctctaga actagtggat cttactggaa actgtgct 38

<210> SEQ ID NO 15
<211> LENGTH: 44
<212> TYPE: DNA

<213> ORGANISM: Artificial Sequence
<220> FEATURE:
<223> OTHER INFORMATION: synthetic_primer

<400> SEQUENCE: 15
tagatcgaaa ggtgcacaaa gatgaaaact ttaaatcatt taaa 44

<210> SEQ ID NO 16
<211> LENGTH: 39
<212> TYPE: DNA
<213> ORGANISM: Artificial Sequence
<220> FEATURE:
<223> OTHER INFORMATION: synthetic_primer

<400> SEQUENCE: 16
ccgctctaga actagtggat cttagtcatg ttgctctac 39

<210> SEQ ID NO 17
<211> LENGTH: 37
<212> TYPE: DNA
<213> ORGANISM: Artificial Sequence
<220> FEATURE:
<223> OTHER INFORMATION: synthetic_primer

<400> SEQUENCE: 17
tagatcgaaa ggtgcacaaa gatgccagat gtaaccg 37

<210> SEQ ID NO 18
<211> LENGTH: 36
<212> TYPE: DNA
<213> ORGANISM: Artificial Sequence
<220> FEATURE:
<223> OTHER INFORMATION: synthetic_primer

<400> SEQUENCE: 18
ccgctctaga actagtggat ctcatgcgga gaaccc 36

<210> SEQ ID NO 19
<211> LENGTH: 36
<212> TYPE: DNA
<213> ORGANISM: Artificial Sequence
<220> FEATURE:
<223> OTHER INFORMATION: synthetic_primer

<400> SEQUENCE: 19
tagatcgaaa ggtgcacaaa gatgcctgat gtgacc 36

<210> SEQ ID NO 20
<211> LENGTH: 36
<212> TYPE: DNA
<213> ORGANISM: Artificial Sequence
<220> FEATURE:
<223> OTHER INFORMATION: synthetic_primer

<400> SEQUENCE: 20
ccgctctaga actagtggat ctcatgcgga gaatcc 36

<210> SEQ ID NO 21
<211> LENGTH: 39
<212> TYPE: DNA
<213> ORGANISM: Artificial Sequence
<220> FEATURE:
<223> OTHER INFORMATION: synthetic_primer

<400> SEQUENCE: 21
tagatcgaaa ggtgcacaaa gatgtcggta cataaagaa 39

-continued

<210> SEQ ID NO 22
<211> LENGTH: 42
<212> TYPE: DNA
<213> ORGANISM: Artificial Sequence
<220> FEATURE:
<223> OTHER INFORMATION: synthetic_primer

<400> SEQUENCE: 22
ccgctctaga actagtggat cttaatattg ttctttttcg tt 42

<210> SEQ ID NO 23
<211> LENGTH: 36
<212> TYPE: DNA
<213> ORGANISM: Artificial Sequence
<220> FEATURE:
<223> OTHER INFORMATION: synthetic_primer

<400> SEQUENCE: 23
tagatcgaaa ggtgcacaaa gatgaaaccc accacc 36

<210> SEQ ID NO 24
<211> LENGTH: 40
<212> TYPE: DNA
<213> ORGANISM: Artificial Sequence
<220> FEATURE:
<223> OTHER INFORMATION: synthetic_primer

<400> SEQUENCE: 24
ccgctctaga actagtggat cttagttgaa agagtgctct 40

<210> SEQ ID NO 25
<211> LENGTH: 40
<212> TYPE: DNA
<213> ORGANISM: Artificial Sequence
<220> FEATURE:
<223> OTHER INFORMATION: synthetic_primer

<400> SEQUENCE: 25
tagatcgaaa ggtgcacaaa gatgtctaca gcaaaaaaag 40

<210> SEQ ID NO 26
<211> LENGTH: 40
<212> TYPE: DNA
<213> ORGANISM: Artificial Sequence
<220> FEATURE:
<223> OTHER INFORMATION: synthetic_primer

<400> SEQUENCE: 26
ccgctctaga actagtggat cttaatactg ttcatcgtca 40

<210> SEQ ID NO 27
<211> LENGTH: 41
<212> TYPE: DNA
<213> ORGANISM: Artificial Sequence
<220> FEATURE:
<223> OTHER INFORMATION: synthetic_primer

<400> SEQUENCE: 27
cttgatatcg aattcctgca ttcagggtag ttgactaaag a 41

<210> SEQ ID NO 28
<211> LENGTH: 17
<212> TYPE: DNA
<213> ORGANISM: Artificial Sequence
<220> FEATURE:

-continued

<223> OTHER INFORMATION: synthetic_primer

<400> SEQUENCE: 28
ctttgtgcac ctttcga 17

<210> SEQ ID NO 29
<211> LENGTH: 40
<212> TYPE: DNA
<213> ORGANISM: Artificial Sequence
<220> FEATURE:
<223> OTHER INFORMATION: synthetic_primer

<400> SEQUENCE: 29
tgaattcgag ctcggtaccc gaaatagcgc ttgatgaatc 40

<210> SEQ ID NO 30
<211> LENGTH: 40
<212> TYPE: DNA
<213> ORGANISM: Artificial Sequence
<220> FEATURE:
<223> OTHER INFORMATION: synthetic_primer

<400> SEQUENCE: 30
ggttgctacc tgcacccggg gggcatgagt atagatgtga 40

<210> SEQ ID NO 31
<211> LENGTH: 40
<212> TYPE: DNA
<213> ORGANISM: Artificial Sequence
<220> FEATURE:
<223> OTHER INFORMATION: synthetic_primer

<400> SEQUENCE: 31
ctatactcat gccccccggg tgcaggtagc aaccacaaag 40

<210> SEQ ID NO 32
<211> LENGTH: 40
<212> TYPE: DNA
<213> ORGANISM: Artificial Sequence
<220> FEATURE:
<223> OTHER INFORMATION: synthetic_primer

<400> SEQUENCE: 32
gtcgactcta gaggatcccc tatgtggcgt tgggtgcagc 40

<210> SEQ ID NO 33
<211> LENGTH: 40
<212> TYPE: DNA
<213> ORGANISM: Artificial Sequence
<220> FEATURE:
<223> OTHER INFORMATION: synthetic_primer

<400> SEQUENCE: 33
catctatact catgcccccc ttcagggtag ttgactaaag 40

<210> SEQ ID NO 34
<211> LENGTH: 40
<212> TYPE: DNA
<213> ORGANISM: Artificial Sequence
<220> FEATURE:
<223> OTHER INFORMATION: synthetic_primer

<400> SEQUENCE: 34
tgtggttgct acctgcaccc ttaatggaaa ctgtgttctt 40

<210> SEQ ID NO 35
<211> LENGTH: 20
<212> TYPE: DNA
<213> ORGANISM: Artificial Sequence
<220> FEATURE:
<223> OTHER INFORMATION: synthetic_primer

<400> SEQUENCE: 35
cccacccggt gtcattcgac 20

<210> SEQ ID NO 36
<211> LENGTH: 19
<212> TYPE: DNA
<213> ORGANISM: Artificial Sequence
<220> FEATURE:
<223> OTHER INFORMATION: synthetic_primer

<400> SEQUENCE: 36
gcgcatccag ctcatcggt 19

<210> SEQ ID NO 37
<211> LENGTH: 264
<212> TYPE: PRT
<213> ORGANISM: Artificial Sequence
<220> FEATURE:
<223> OTHER INFORMATION: synthetic_PanB WT

<400> SEQUENCE: 37

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Gly Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr

-continued 245 250 255

Pro Gly Glu Glu His Ser Phe His
260

<210> SEQ ID NO 38
<211> LENGTH: 40
<212> TYPE: DNA
<213> ORGANISM: Artificial Sequence
<220> FEATURE:
<223> OTHER INFORMATION: synthetic_primer

<400> SEQUENCE: 38
gtttctacca gccactcgga gccttcaatt ttgaccatgt 40

<210> SEQ ID NO 39
<211> LENGTH: 40
<212> TYPE: DNA
<213> ORGANISM: Artificial Sequence
<220> FEATURE:
<223> OTHER INFORMATION: synthetic_primer

<400> SEQUENCE: 39
acatggtcaa aattgaaggc tccgagtggc tggtagaaac 40

<210> SEQ ID NO 40
<211> LENGTH: 40
<212> TYPE: DNA
<213> ORGANISM: Artificial Sequence
<220> FEATURE:
<223> OTHER INFORMATION: synthetic_primer

<400> SEQUENCE: 40
gtttctacca gccactcgca gccttcaatt ttgaccatgt 40

<210> SEQ ID NO 41
<211> LENGTH: 40
<212> TYPE: DNA
<213> ORGANISM: Artificial Sequence
<220> FEATURE:
<223> OTHER INFORMATION: synthetic_primer

<400> SEQUENCE: 41
acatggtcaa aattgaaggc tgcgagtggc tggtagaaac 40

<210> SEQ ID NO 42
<211> LENGTH: 40
<212> TYPE: DNA
<213> ORGANISM: Artificial Sequence
<220> FEATURE:
<223> OTHER INFORMATION: synthetic_primer

<400> SEQUENCE: 42
gtttctacca gccactccag gccttcaatt ttgaccatgt 40

<210> SEQ ID NO 43
<211> LENGTH: 40
<212> TYPE: DNA
<213> ORGANISM: Artificial Sequence
<220> FEATURE:
<223> OTHER INFORMATION: synthetic_primer

<400> SEQUENCE: 43
acatggtcaa aattgaaggc ctggagtggc tggtagaaac 40

<210> SEQ ID NO 44

<211> LENGTH: 40
<212> TYPE: DNA
<213> ORGANISM: Artificial Sequence
<220> FEATURE:
<223> OTHER INFORMATION: synthetic_primer

<400> SEQUENCE: 44
gtttctacca gccactcgat gccttcaatt ttgaccatgt 40

<210> SEQ ID NO 45
<211> LENGTH: 40
<212> TYPE: DNA
<213> ORGANISM: Artificial Sequence
<220> FEATURE:
<223> OTHER INFORMATION: synthetic_primer

<400> SEQUENCE: 45
acatggtcaa aattgaaggc atcgagtggc tggtagaaac 40

<210> SEQ ID NO 46
<211> LENGTH: 40
<212> TYPE: DNA
<213> ORGANISM: Artificial Sequence
<220> FEATURE:
<223> OTHER INFORMATION: synthetic_primer

<400> SEQUENCE: 46
gtttctacca gccactcggt gccttcaatt ttgaccatgt 40

<210> SEQ ID NO 47
<211> LENGTH: 40
<212> TYPE: DNA
<213> ORGANISM: Artificial Sequence
<220> FEATURE:
<223> OTHER INFORMATION: synthetic_primer

<400> SEQUENCE: 47
acatggtcaa aattgaaggc accgagtggc tggtagaaac 40

<210> SEQ ID NO 48
<211> LENGTH: 40
<212> TYPE: DNA
<213> ORGANISM: Artificial Sequence
<220> FEATURE:
<223> OTHER INFORMATION: synthetic_primer

<400> SEQUENCE: 48
gtttctacca gccactccac gccttcaatt ttgaccatgt 40

<210> SEQ ID NO 49
<211> LENGTH: 40
<212> TYPE: DNA
<213> ORGANISM: Artificial Sequence
<220> FEATURE:
<223> OTHER INFORMATION: synthetic_primer

<400> SEQUENCE: 49
acatggtcaa aattgaaggc gtggagtggc tggtagaaac 40

<210> SEQ ID NO 50
<211> LENGTH: 40
<212> TYPE: DNA
<213> ORGANISM: Artificial Sequence
<220> FEATURE:
<223> OTHER INFORMATION: synthetic_primer

<400> SEQUENCE: 50

-continued gtttctacca gccactccat gccttcaatt ttgaccatgt 40

<210> SEQ ID NO 51
<211> LENGTH: 40
<212> TYPE: DNA
<213> ORGANISM: Artificial Sequence
<220> FEATURE:
<223> OTHER INFORMATION: synthetic_primer

<400> SEQUENCE: 51
acatggtcaa aattgaaggc atggagtggc tggtagaaac 40

<210> SEQ ID NO 52
<211> LENGTH: 40
<212> TYPE: DNA
<213> ORGANISM: Artificial Sequence
<220> FEATURE:
<223> OTHER INFORMATION: synthetic_primer

<400> SEQUENCE: 52
gtttctacca gccactcatc gccttcaatt ttgaccatgt 40

<210> SEQ ID NO 53
<211> LENGTH: 40
<212> TYPE: DNA
<213> ORGANISM: Artificial Sequence
<220> FEATURE:
<223> OTHER INFORMATION: synthetic_primer

<400> SEQUENCE: 53
acatggtcaa aattgaaggc gatgagtggc tggtagaaac 40

<210> SEQ ID NO 54
<211> LENGTH: 40
<212> TYPE: DNA
<213> ORGANISM: Artificial Sequence
<220> FEATURE:
<223> OTHER INFORMATION: synthetic_primer

<400> SEQUENCE: 54
gtttctacca gccactcttc gccttcaatt ttgaccatgt 40

<210> SEQ ID NO 55
<211> LENGTH: 40
<212> TYPE: DNA
<213> ORGANISM: Artificial Sequence
<220> FEATURE:
<223> OTHER INFORMATION: synthetic_primer

<400> SEQUENCE: 55
acatggtcaa aattgaaggc gaagagtggc tggtagaaac 40

<210> SEQ ID NO 56
<211> LENGTH: 40
<212> TYPE: DNA
<213> ORGANISM: Artificial Sequence
<220> FEATURE:
<223> OTHER INFORMATION: synthetic_primer

<400> SEQUENCE: 56
gtttctacca gccactcgtt gccttcaatt ttgaccatgt 40

<210> SEQ ID NO 57
<211> LENGTH: 40
<212> TYPE: DNA

<213> ORGANISM: Artificial Sequence
<220> FEATURE:
<223> OTHER INFORMATION: synthetic_primer

<400> SEQUENCE: 57
acatggtcaa aattgaaggc aacgagtggc tggtagaaac 40

<210> SEQ ID NO 58
<211> LENGTH: 40
<212> TYPE: DNA
<213> ORGANISM: Artificial Sequence
<220> FEATURE:
<223> OTHER INFORMATION: synthetic_primer

<400> SEQUENCE: 58
gtttctacca gccactcctg gccttcaatt ttgaccatgt 40

<210> SEQ ID NO 59
<211> LENGTH: 40
<212> TYPE: DNA
<213> ORGANISM: Artificial Sequence
<220> FEATURE:
<223> OTHER INFORMATION: synthetic_primer

<400> SEQUENCE: 59
acatggtcaa aattgaaggc caggagtggc tggtagaaac 40

<210> SEQ ID NO 60
<211> LENGTH: 40
<212> TYPE: DNA
<213> ORGANISM: Artificial Sequence
<220> FEATURE:
<223> OTHER INFORMATION: synthetic_primer

<400> SEQUENCE: 60
gtttctacca gccactctgc gccttcaatt ttgaccatgt 40

<210> SEQ ID NO 61
<211> LENGTH: 40
<212> TYPE: DNA
<213> ORGANISM: Artificial Sequence
<220> FEATURE:
<223> OTHER INFORMATION: synthetic_primer

<400> SEQUENCE: 61
acatggtcaa aattgaaggc gcagagtggc tggtagaaac 40

<210> SEQ ID NO 62
<211> LENGTH: 264
<212> TYPE: PRT
<213> ORGANISM: Artificial Sequence
<220> FEATURE:
<223> OTHER INFORMATION: synthetic_PanB with G116A mutation

<400> SEQUENCE: 62

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
```

```
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Ala Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 63
<211> LENGTH: 264
<212> TYPE: PRT
<213> ORGANISM: Artificial Sequence
<220> FEATURE:
<223> OTHER INFORMATION: synthetic_PanB with G116N mutation

<400> SEQUENCE: 63

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Asn Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
```

-continued

```
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 64
<211> LENGTH: 264
<212> TYPE: PRT
<213> ORGANISM: Artificial Sequence
<220> FEATURE:
<223> OTHER INFORMATION: synthetic_PanB with G116T mutation

<400> SEQUENCE: 64

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Thr Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
```

260

<210> SEQ ID NO 65
<211> LENGTH: 264
<212> TYPE: PRT
<213> ORGANISM: Artificial Sequence
<220> FEATURE:
<223> OTHER INFORMATION: synthetic_PanB with G116E mutation

<400> SEQUENCE: 65

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Glu Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr
245 250 255

Pro Gly Glu Glu His Ser Phe His
260

<210> SEQ ID NO 66
<211> LENGTH: 264
<212> TYPE: PRT
<213> ORGANISM: Artificial Sequence
<220> FEATURE:
<223> OTHER INFORMATION: synthetic_PanB with G116S mutation

<400> SEQUENCE: 66

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Ser Glu Trp Leu Val Glu Thr Val Gln Met Leu Thr Glu
115 120 125

Arg Ala Val Pro Val Cys Gly His Leu Gly Leu Thr Pro Gln Ser Val
130 135 140

Asn Ile Phe Gly Gly Tyr Lys Val Gln Gly Arg Gly Asp Glu Ala Gly
145 150 155 160

Asp Gln Leu Leu Ser Asp Ala Leu Ala Leu Glu Ala Ala Gly Ala Gln
165 170 175

Leu Leu Val Leu Glu Cys Val Pro Val Glu Leu Ala Lys Arg Ile Thr
180 185 190

Glu Ala Leu Ala Ile Pro Val Ile Gly Ile Gly Ala Gly Asn Val Thr
195 200 205

Asp Gly Gln Ile Leu Val Met His Asp Ala Phe Gly Ile Thr Gly Gly
210 215 220

His Ile Pro Lys Phe Ala Lys Asn Phe Leu Ala Glu Thr Gly Asp Ile
225 230 235 240

Arg Ala Ala Val Arg Gln Tyr Met Ala Glu Val Glu Ser Gly Val Tyr
245 250 255

Pro Gly Glu Glu His Ser Phe His
260

<210> SEQ ID NO 67
<211> LENGTH: 264
<212> TYPE: PRT
<213> ORGANISM: Artificial Sequence
<220> FEATURE:
<223> OTHER INFORMATION: synthetic_PanB with G116V mutation

<400> SEQUENCE: 67

Met Lys Pro Thr Thr Ile Ser Leu Leu Gln Lys Tyr Lys Gln Glu Lys
1 5 10 15

Lys Arg Phe Ala Thr Ile Thr Ala Tyr Asp Tyr Ser Phe Ala Lys Leu
20 25 30

Phe Ala Asp Glu Gly Leu Asn Val Met Leu Val Gly Asp Ser Leu Gly
35 40 45

Met Thr Val Gln Gly His Asp Ser Thr Leu Pro Val Thr Val Ala Asp
50 55 60

Ile Ala Tyr His Thr Ala Ala Val Arg Arg Gly Ala Pro Asn Cys Leu
65 70 75 80

Leu Leu Ala Asp Leu Pro Phe Met Ala Tyr Ala Thr Pro Glu Gln Ala
85 90 95

Phe Glu Asn Ala Ala Thr Val Met Arg Ala Gly Ala Asn Met Val Lys
100 105 110

Ile Glu Gly Val Glu Trp Leu Val Glu Thr Val Gln Met Leu Thr Glu
115 120 125

-continued

```
Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

```
<210> SEQ ID NO 68
<211> LENGTH: 264
<212> TYPE: PRT
<213> ORGANISM: Artificial Sequence
<220> FEATURE:
<223> OTHER INFORMATION: synthetic_PanB with G116I mutation

<400> SEQUENCE: 68

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Ile Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220
```

```
His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 69
<211> LENGTH: 264
<212> TYPE: PRT
<213> ORGANISM: Artificial Sequence
<220> FEATURE:
<223> OTHER INFORMATION: synthetic_PanB with G116L mutation

<400> SEQUENCE: 69

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Leu Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 70
<211> LENGTH: 264
<212> TYPE: PRT
<213> ORGANISM: Artificial Sequence
<220> FEATURE:
<223> OTHER INFORMATION: synthetic_PanB with G116D mutation

<400> SEQUENCE: 70
```

-continued

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Asp Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 71
<211> LENGTH: 264
<212> TYPE: PRT
<213> ORGANISM: Artificial Sequence
<220> FEATURE:
<223> OTHER INFORMATION: synthetic_PanB with G116C mutation

<400> SEQUENCE: 71

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95
```

```
Phe Glu Asn Ala Ala Thr Val Met Arg Ala Gly Ala Asn Met Val Lys
            100                 105                 110

Ile Glu Gly Cys Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

<210> SEQ ID NO 72
<211> LENGTH: 264
<212> TYPE: PRT
<213> ORGANISM: Artificial Sequence
<220> FEATURE:
<223> OTHER INFORMATION: synthetic_PanB with G116Q mutation

<400> SEQUENCE: 72

```
Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gln Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190
```

```
Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260


<210> SEQ ID NO 73
<211> LENGTH: 264
<212> TYPE: PRT
<213> ORGANISM: Artificial Sequence
<220> FEATURE:
<223> OTHER INFORMATION: synthetic_PanB with G116M mutation

<400> SEQUENCE: 73

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Met Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Asp Glu Ala Gly
145                 150                 155                 160

Asp Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Glu Ser Gly Val Tyr
                245                 250                 255

Pro Gly Glu Glu His Ser Phe His
            260
```

MICROORGANISM HAVING INCREASED ACTIVITY OF 3-METHYL-2-OXOBUTANOATE HYDROXYMETHYLTRANSFERASE, AND USE THEREOF

CROSS-REFERENCE TO RELATED APPLICATIONS

This application claims the benefit of KR 10-2020-0081194 filed on Jul. 1, 2020 with the Korean Intellectual Property Office, the entire disclosure of which is herein incorporated by reference.

TECHNICAL FIELD

Provided are a polypeptide having an activity of 3-methyl-2-oxobutanoate hydroxymethyltransferase, a microorganism having enhanced activity of 3-methyl-2-oxobutanoate hydroxymethyltransferase, a composition for production of pantothenic acid and/or pantoic acid comprising the polypeptide and/or microorganism, and a method of producing pantothenic acid and/or pantoic acid comprising culturing the microorganism.

BACKGROUND ART

Pantothenic acid, which is also called vitamin B5, is a substance belonging to vitamin B complex and one of commercially important substances that are variously applied to cosmetics, medicine, human nutrition, animal nutrition, and the like. Pantothenic acid has a structure in which beta-alanine is linked to pantonic acid by an amide bond.

Pantothenic acid or pantonic acid may be prepared by chemical synthesis or biotechnologically by fermenting a suitable microorganism in a suitable medium. An advantage of biotechnological preparation methods using microorganisms is that the desired stereo-isomeric D-form of pantothenic acid or pantosan is formed.

Accordingly, it is required to develop a microorganism having an advantageous effect in biotechnologically producing pantothenic acid and/or pantoic acid and a technology for producing pantothenic acid and/or pantoic acid with high efficiency using the same.

PRIOR ART DOCUMENTS

Patent Documents

U.S. Pat. No. 7,718,205 B2 (published on 2010 May 18)

DISCLOSURE

Technical Problem

An embodiment of the present disclosure provides a polypeptide having an activity of 3-methyl-2-oxobutanoate hydroxymethyltransferase. For example, the polypeptide may comprise the amino acid sequence of SEQ ID NO: 37 or an amino acid sequence in which an amino acid corresponding to position 116 of the amino acid sequence of SEQ ID NO: 37 is substituted with other amino acid.

Another embodiment provides a polynucleotide encoding the polypeptide.

Another embodiment provides a recombinant vector comprising the polynucleotide. The recombinant vector may be an expression vector for expressing the polynucleotide.

Another embodiment provides a microorganism that has enhanced activity of 3-methyl-2-oxobutanoate hydroxymethyltransferase and produces pantothenic acid and/or pantoic acid.

Another embodiment provides a composition for production of pantothenic acid and/or pantoic acid, the composition comprising at least one selected from the group consisting of the polypeptide, the polynucleotide, the recombinant vector, and the microorganism.

Another embodiment provides a method of producing pantothenic acid and/or pantoic acid, comprising culturing the microorganism.

Another embodiment provides a use of the polypeptide, the polynucleotide, the recombinant vector, and the microorganism in producing pantothenic acid and/or pantoic acid.

Technical Solution

In the present disclosure, 3-methyl-2-oxobutanoate hydroxymethyltransferase or a variant thereof that is capable of improving ability of pantothenic acid and/or pantoic acid production is searched and introduced into a microorganism, whereby a recombinant microorganism having excellent ability of pantothenic acid and/or pantoic acid production is provided.

In the present disclosure, it is confirmed that a microorganism expressing 3-methyl-2-oxobutanoate hydroxymethyltransferase derived from *E. coli* has excellent pantothenic acid production ability, and it is also confirmed that the pantothenic acid production ability is more increased, when an amino acid substitution mutation is introduced at a specific position of the 3-methyl-2-oxobutanoate hydroxymethyltransferase derived from *E. coli.*

An embodiment provides a polypeptide having an activity of 3-methyl-2-oxobutanoate hydroxymethyltransferase. The polypeptide may be a hydroxymethyltransferase derived from *E. coli* or a variant thereof. For example, the polypeptide may comprise the amino acid sequence of SEQ ID NO: 37 or an amino acid sequence in which an amino acid corresponding to position 116 of the amino acid sequence of SEQ ID NO: 37 is substituted with other amino acid.

Another embodiment provides a polynucleotide encoding the polypeptide.

Another embodiment provides a recombinant vector carrying the polynucleotide. The recombinant vector may be used as an expression vector of the polynucleotide.

Another embodiment provides a microorganism that has enhanced activity of 3-methyl-2-oxobutanoate hydroxymethyltransferase. The microorganism may produce pantothenic acid and/or pantoic acid. The hydroxymethyltransferase may be a hydroxymethyltransferase derived from *E. coli* or a variant thereof. For example, the hydroxymethyltransferase may comprise the amino acid sequence of SEQ ID NO: 37 or an amino acid sequence in which an amino acid corresponding to position 116 of the amino acid sequence of SEQ ID NO: 37 is substituted with other amino acid.

The microorganism having enhanced activity of 3-methyl-2-oxobutanoate hydroxymethyltransferase may have increased ability of producing pantothenic acid and/or pantoic acid, compared with a microorganism that is not subjected to an enhancement of 3-methyl-2-oxobutanoate hydroxymethyltransferase activity and belongs to the same species.

Another embodiment provides a composition for production of pantothenic acid and/or pantoic acid, the composition comprising at least one selected from the group consisting of the polypeptide, the polynucleotide, the recombinant vector, and the microorganism having enhanced 3-methyl-2-oxobutanoate hydroxymethyltransferase activity.

Another embodiment provides a method of producing pantothenic acid and/or pantoic acid, comprising culturing the microorganism having enhanced 3-methyl-2-oxobutanoate hydroxymethyltransferase activity.

Another embodiment provides a use of the polypeptide, the polynucleotide, the recombinant vector, and the microorganism having enhanced 3-methyl-2-oxobutanoate hydroxymethyltransferase activity in producing pantothenic acid and/or pantoic acid.

A detailed description will be given of the present disclosure.

In the present disclosure, the pantothenic acid (e.g., D-pantothenic acid), which is a compound having a structure of chemical formula 1, is a vitamin (vitamin B5) wherein β-alanine is coupled to pantoic acid by an amide bond. In addition, the pantothenic acid is a component of coenzyme A (CoA) and acyl carrier protein, ACP), and involved in various metabolisms of living bodies.

(Chemical formula 1 pantothenic acid)

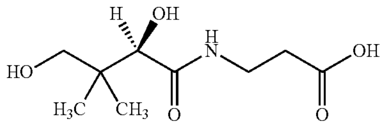

The pantoic acid (e.g., D-pantoic acid) is a compound having a structure of chemical formula 2, and acts as a component of various biologically active compounds:

(Chemical formula 2 pantoic acid)

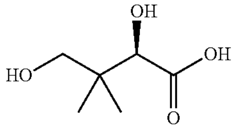

In the present disclosure, the 3-methyl-2-oxobutanoate hydroxymethyltransferase is an enzyme that catalyzes a biosynthesis of tetrahydrofolate and 2-dehydropantoate from 5,10-methylentetrahydrofolate, 3-methyl-2-oxobutanoate, and water.

In the present disclosure, the microorganism having enhanced 3-methyl-2-oxobutanoate hydroxymethyltransferase activity may be a microorganism in which a 3-methyl-2-oxobutanoate hydroxymethyltransferase coding gene is introduced.

In a specific embodiment, the 3-methyl-2-oxobutanoate hydroxymethyltransferase is an *E. coli*-derived 3-methyl-2-oxobutanoate hydroxymethyltransferase (wild-type) or a variant thereof that is mutated by substitution, deletion, or insertion of at least one amino acid.

The wild-type *E. coli*-derived 3-methyl-2-oxobutanoate hydroxymethyltransferase may comprise the amino acid sequence of SEQ ID NO: 37.

In an embodiment, the variant of the 3-methyl-2-oxobutanoate hydroxymethyltransferase may be a polypeptide wherein an amino acid corresponding to position 116 of *E. coli* 3-methyl-2-oxobutanoate hydroxymethyltransferase consisting of the amino acid sequence of SEQ ID NO: 37 is substituted with other amino acid, which is selected from the group consisting of alanine (A, Ala), asparagine (N, Asn), threonine (T, Thr), glutamic acid (E, Glu), serine (S, Ser), valine (V, Val), isoleucine (I, Ile), leucine (L, Leu), aspartic acid (D, Asp), cysteine (C, Cys), glutamine (Q, Gln), methionine (M, Met), phenylalanine (F, Phe), proline (P, Pro), tryptophan (W, Trp), tyrosine (Y, Tyr), arginine (R, Arg), histidine (H, His), lysine (K, Lys), and glycine (G, Gly), and different from the original amino acid. In a specific embodiment, the variant of the 3-methyl-2-oxobutanoate hydroxymethyltransferase may be a polypeptide wherein an amino acid corresponding to position 116 of the amino acid sequence of SEQ ID NO: 37 is substituted with other amino acid selected from the group consisting of alanine (A, Ala), asparagine (N, Asn), threonine (T, Thr), glutamic acid (E, Glu), serine (S, Ser), valine (V, Val), isoleucine (I, Ile), leucine (L, Leu), aspartic acid (D, Asp), cysteine (C, Cys), glutamine (Q, Gln), and methionine (M, Met). When the variant is further modified by deletion, substitution, modification, and/or insertion at a partial amino acid sequence other than the amino acid corresponding to position 116 of the amino acid sequence of SEQ ID NO: 37, the partially further modified variant may also be encompassed within the scope of the variants of the present disclosure, so long as the variant possesses an activity of 3-methyl-2-oxobutanoate hydroxymethyltransferase and/or an activity of increasing or conferring production ability of pantothenic acid and/or pantoic acid in a cell (a microorganism).

In an embodiment, the variant may comprise a polypeptide having sequence homology or identity of 80% or more, 85% or more, 90% or more, 91% or more, 92% or more, 93% or more, 94% or more, 95% or more, 96% or more, 97% or more, 98% or more, or 99% or more with the amino acid sequence of SEQ ID NO: 37 and modified at an amino acid corresponding to position 116 of the amino acid sequence of SEQ ID NO: 37 by substitution with other amino acid. That is, a polypeptide, which (1) is modified at an amino acid corresponding to position 116 of the amino acid sequence of SEQ ID NO: 37 by substitution with other amino acid, (2) has sequence homology or identity of 80% or more, 90% or more, 95% or more, 96% or more, 97% or more, 98% or more, or 99% or more, and less than 100%, with the amino acid sequence of SEQ ID NO: 37, and (3) possesses an activity of 3-methyl-2-oxobutanoate hydroxymethyltransferase and/or an activity of increasing or conferring production ability of pantothenic acid and/or pantoic acid in a cell (a microorganism), may be included within the scope of the variants of the present disclosure.

In a specific embodiment, the variant of 3-methyl-2-oxobutanoate hydroxymethyltransferase may comprise a polypeptide comprising an amino acid sequence selected from the group consisting of SEQ ID NO: 62 to SEQ ID NO: 73, but not be limited thereto. When the polypeptide consisting of an amino acid sequence selected from the group consisting of SEQ ID NO: 62 to SEQ ID NO: 73 is modified by deletion, substitution, modification, and/or insertion at a partial amino acid sequence other than the amino acid of position 116, the partially modified polypeptide may also be encompassed within the scope of the variants of the present disclosure, so long as the polypeptide possesses an activity of 3-methyl-2-oxobutanoate hydroxymethyltransferase and/or an activity of increasing or conferring production ability of pantothenic acid and/or pantoic acid in a cell (a microorganism). In addition, the variant may comprise a polypeptide, wherein the amino acid corresponding to position 116 of the amino acid sequence of SEQ ID NO: 37 in the amino acid sequence selected from SEQ ID NO: 62 to SEQ ID NO: 73 is fixed, and the polypeptide has sequence homology or identity of 80% or more, 85% or more, 90% or more, 91% or more, 92% or more, 93% or more, 94% or more, 95% or more, 96% or more, 97% or more, 98% or more, or 99% or more with the amino acid sequence selected from SEQ ID NO: 62 to SEQ ID NO: 73. For example, a polypeptide, which is modified from SEQ ID NO: 37 by substitution of an amino acid corresponding to position 116 of the amino acid sequence of SEQ ID NO: 37 with other amino acid, and has sequence homology or identity of 80% or more, 85% or more, 90% or more, 91% or more, 92% or more, 93% or more, 94% or more, 95% or more, 96% or more, 97% or more, 98% or more, or 99% or more, and less than 100%, with the amino acid sequence selected from SEQ ID NO: 62 to SEQ ID NO: 73, and exhibits an activity of 3-methyl-2-oxobutanoate hydroxymethyltransferase and/or an activity of increasing or conferring production ability of pantothenic acid and/or pantoic acid in a cell (a microorganism), may be included within the scope of the variants of the present disclosure.

In the present disclosure, the term "microorganism having enhanced 3-methyl-2-oxobutanoate hydroxymethyltransferase activity" may be a microorganism which is manipulated (mutated) so as to express the polypeptide exhibiting 3-methyl-2-oxobutanoate hydroxymethyltransferase activity as aforementioned, whereby the microorganism that does not possess production ability of pantothenic acid and/or pantoic acid becomes having production ability of pantothenic acid and/or pantoic acid, or the microorganism has higher production ability of pantothenic acid and/or pantoic acid than its inherent production ability of pantothenic acid and/or pantoic acid. In the present disclosure, the term "microorganism" may encompass single cell bacteria, and be interchangeable with "cell". In the present disclosure, a microorganism that is not modified or before being modified so as to express the polypeptide exhibiting 3-methyl-2-oxobutanoate hydroxymethyltransferase activity may be expressed as a parent microorganism (or parent strain) or host cell, in order to being distinguished from the modified microorganism.

In the present disclosure, the microorganism may be at least one selected from the group consisting of microorganisms belonging to genus *Corynebacterium*, genus *Escherichia*, and the like. The microorganism belonging to genus *Corynebacterium* may include *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, and the like, but not be limited thereto. More specifically, the microorganism belonging to genus *Corynebacterium* may be *Corynebacterium glutamicum*. The microorganism belonging to genus *Escherichia* may be *Escherichia coli*.

In the present disclosure, the term "microorganism having enhanced activity of 3-methyl-2-oxobutanoate hydroxymethyltransferase" may refer to a microorganism expressing a polypeptide having a 3-methyl-2-oxobutanoate hydroxymethyltransferase activity, which is modified (manipulated) from a parent strain so as to express a polypeptide having a 3-methyl-2-oxobutanoate hydroxymethyltransferase activity. In an embodiment, the mutation so as to expressing a polypeptide having a 3-methyl-2-oxobutanoate hydroxymethyltransferase activity may be performed by introducing a polynucleotide encoding the polypeptide having a 3-methyl-2-oxobutanoate hydroxymethyltransferase activity as described above or a recombinant vector comprising the polynucleotide into a parent strain. The polynucleotide encoding the polypeptide having a 3-methyl-2-oxobutanoate hydroxymethyltransferase activity, which is introduced into a parent strain, may be one replacing an endogenous 3-methyl-2-oxobutanoate hydroxymethyltransferase gene of the parent strain or one further comprised in addition to the endogenous gene.

In a specific embodiment, the microorganism expressing the polypeptide with 3-methyl-2-oxobutanoate hydroxymethyltransferase activity may be the microorganism deposited under accession number KCCM12744P.

In the present disclosure, with respect to a polynucleotide (used interchangeably with "gene") or a polypeptide (used interchangeably with "protein"), the wordings "comprising a specific nucleic acid or amino acid sequence", "consisting of a specific nucleic acid or amino acid sequence", and "being represented as a specific nucleic acid or amino acid sequence" are interchangeable expressions with the equivalent meanings that the polynucleotide or polypeptide essentially comprises the specific nucleic acid or amino acid sequence. Further, these wordings may be construed as "comprising a substantially equivalent sequence" (or as "not excluding introduction of the following mutation"), which results from a mutation (deletion, substitution, modification, and/or addition) to the specific nucleic acid or amino acid sequence insofar as the polynucleotide or polypeptide retains its original function and/or desired function.

In an embodiment, the nucleic acid sequence or amino acid sequence provided in the present disclosure may comprise mutants thereof obtained by conventional mutation methods, for example, direct evolution and/or site-directed mutagenesis insofar as the mutants retain the original function or desired function of the sequence. In an embodiment, the expression that a polynucleotide or polypeptide "comprises or consists of a specific nucleic acid or amino acid sequence" may mean that a polynucleotide or polypeptide essentially comprises or consists essentially of (i) the specific nucleic acid or amino acid sequence, or (ii) a nucleic acid or amino acid sequence having a sequence identity of 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.5% or greater, or 99.9% or greater, wherein the polynucleotide or polypeptide retains its original function and/or desired function. As used herein, the term "original function" may mean a function of increasing or conferring an ability of producing pantothenic acid and/or pantoic acid.

For the nucleotide sequences described in the present disclosure, various modifications can be made in the coding regions insofar as they do not change amino acid sequences and/or functions of the polypeptide expressed from the coding regions, due to codon degeneracy or in consideration of the codons preferred by the microorganisms in which the protein are to be expressed.

In this disclosure, the terms "identity" or "homology" may refer to the degree of relation between two given amino acid sequences or nucleic acid sequences and may be expressed as a percentage (%). For an identity between nucleic acid sequences, the percentage thereof can be determined using, for example, the algorithm BLAST (see Karlin and Altschul, Pro. Natl. Acad. Sci. USA, 90, 5873 (1993)) or FASTA by Pearson (see Methods Enzymol., 183, 63 (1990)). Programs called BLASTN and BLASTX have been developed on the basis of the algorithm BLAST (see http://www.ncbi.nlm.nih.gov).

In an embodiment, a polynucleotide comprising a specific nucleic acid sequence provided herein may be construed to comprise a polynucleotide containing a nucleic acid sequence complementary to the specific nucleic acid sequence as well as a polynucleotide containing the specific nucleic acid sequence or a substantially equivalent nucleic acid sequence thereto. In detail, the complementary polynucleotides can be hybridized at properly adjustable Tm values, for example, at a Tm of 55° C., 60° C., 63° C., or 65° C. according to purposes and can be analyzed in the following condition: such conditions are described in detail in known documents. For example, mentions may be made of a condition in which hybridization is made between genes if their homology is 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 98% or greater, 99.5% or greater, or 99.9% or greater, but not made if their homology is lower than the values or a typical condition for southern hybridization under which one or more, in detail, two or three washes are performed at the temperature and salt concentration of 60° C., 1×SSC (saline-sodium citrate buffer), and 0.1% (w/v) SDS (sodium dodecyl sulfate); 60° C., 0.1×SSC, and 0.1% SDS; or 68° C., 0.1×SSC, and 0.1% SDS, but without limitations thereto. For hybridization, two polynucleotides are required to have complementary sequences to each other. Depending on hybridization stringency, a mismatch or mismatches may be allowed between bases. The term "complementary" may be used to describe a relationship between nucleotide bases that can match up with each other. For DNA, for instance, adenosine is complementary to thymine and cytosine is complementary to guanine. Proper hybridization stringency for polynucleotides may vary, depending on various factors comprising polynucleotide length and complementarity and is well known in the art (see Sambrook et al., 9.50-9.51, 11.7-11.8).

For the incorporation of a gene or a vector, a person skilled in the art could appropriately adopt a transformation method known in the art. As used herein, the term "transformation" may refer to an action by which a vector carrying a polynucleotide coding fora target protein (e.g., a polypeptide exhibiting an activity of 3-methyl-2-oxobutanoate hydroxymethyltransferase and/or an activity of increasing or conferring production ability of pantothenic acid and/or pantoic acid, as aforementioned) is introduced into a host microorganism to express the protein encoded by the polynucleotide in the host cell. The introduced polynucleotide may be located inside or outside the chromosome of the host microorganism as long as it is expressed in the host microorganism. In addition, the polynucleotide comprises a DNA or an RNA coding for a target protein. So long as it enables the introduction and expression of the polynucleotide in a host microorganism, any delivery means may be employed. For example, a polynucleotide may take a form of an expression cassette that comprises all the elements necessary for autonomous expression in order that the polynucleotide is introduced into a host cell. The expression cassette may conventionally comprise expression regulatory elements operably linked to the polynucleotide, such as a promoter, a transcription stop signal, a ribosome binding site, and/or a translation stop signal. The expression cassette may be an expression vector that can replicate by itself. In addition, the polynucleotide per se may be introduced into a host cell and may be operably linked to a sequence necessary for expression in the host cell. As used herein, the term "operably linked" means a functional connection between an expression regulatory element (e.g., promoter) and the polynucleotide so that the expression regulatory element can control (e.g., initiate) the transcription of the polynucleotide encoding a target protein (e.g., a polypeptide exhibiting an activity of 3-methyl-2-oxobutanoate hydroxymethyltransferase and/or an activity of increasing or conferring production ability of pantothenic acid and/or pantoic acid, as aforementioned). An operable linkage can be accomplished using a genetic recombination technology known in the art, for example, typical site-specific DNA cleavage and ligation, but without limitations thereto.

For transformation of a host cell, any method may be employed as long as it allows the transformation of nucleic acids into the host microorganism. Transformation techniques known in the art could be properly selected according to host microorganisms. Examples of the transformation techniques known in the art may include electroporation, calcium phosphate ($CaPO_4$) precipitation, calcium chloride ($CaCl_2$) precipitation, microinjection, polyethylene glycol (PEG)-mediated uptake, DEAE-dextran-mediated delivery, cationic liposome method, lipofection, and lithium acetate-DMSO method, but are not limited thereto.

A person skilled in the art could select a suitable method for incorporating a polynucleotide into a genome (chromosome) in a cell. For example, the incorporation may be accomplished using an RNA-guided endonuclease system (or CRISPR system); for example, the RNA-guided endonuclease system may be at least one selected from the group consisting of: a mixture of (a) RNA-guided endonuclease (e.g., Cas9 protein, etc.), a gene coding therefor, or a vector carrying the gene; and (b) guide RNA (i.e., single guide RNA (sgRNA), etc.), DNA coding therefor, or a vector carrying the DNA (e.g., a mixture of RNA-guided endonuclease protein and guide RNA), a complex (e.g., ribonucleoprotein (RNP)), a recombinant vector (e.g., a vector comprising RNA-guided endonuclease encoding gene and a DNA coding for guide RNA together, etc.), and the like, but without limitations thereto.

As used herein, the term "vector" may refer to a DNA construct containing a target protein-encoding nucleotide sequence which is operably linked to a suitable regulatory sequence capable of effecting the expression of the target protein in a suitable host. The regulatory sequences may comprise a promoter to initiate transcription, an optional operator sequence to regulate such transcription, a sequence encoding suitable mRNA ribosome binding sites, and/or sequences which regulate termination of transcription and/or translation. Once transformed into a suitable host cell, the vector may be expressed independently of the genome of the host cell or may integrate into the genome of the host cell.

So long as it replicates in a host cell, any vector can be employed herein with no particular limitations imparted thereto. It may be selected from among commonly used vectors. Examples of such commonly used vectors may include plasmids, cosmids, viruses, and bacteriophages, which may be in natural or recombinant states. For instance, the phage vector or cosmid vector is exemplified by pWE15, M13, MBL3, MBL4, IXII, ASHII, APII, t10, t11, Charon4A, Charon21A, and the like. The plasmid vectors may be derived from one selected from pBR-, pUC-, pBluescriptll-, pGEM-, pTZ-, pCL- and pET-lineages. Examples of the vector may include, but not be limited to, pDZ, pACYC177, pACYC184, pCL, pECCG117, pUC19, pBR322, pMW118, pCC1BAC, and the like.

A vector available herein may be a known expression vector and/or a vector for incorporating a polynucleotide into a chromosome of a host cell. The incorporation of a polynucleotide into a chromosome of a host cell may be achieved using any method known in the art, for example, homologous recombination, but with no limitations thereto. The vector may further carry a selection marker for determining whether a gene of interest is incorporated into a chromosome. The selection marker is to select a cell transformed with the vector, that is, to determine the incorporation of the polypeptide and may be selected from among genes that confer selectable phenotypes, such as drug resistance, auxotrophy, cytoxic drug resistance, and expression surface proteins. Under the circumstance where a selective agent is applied to cells, only the cells capable of expressing a selection marker can survive or express a distinctive phenotype so that the transformed cells can be selected.

Another embodiment provide a method of increasing a pantothenic acid and/or pantoic acid production ability in a microorganism or conferring a pantothenic acid and/or pantoic acid production ability to a microorganism, the method comprising a step of activating a 3-methyl-2-oxobutanoate hydroxymethyltransferase activity of the microorganism.

The step of activating the 3-methyl-2-oxobutanoate hydroxymethyltransferase activity of the microorganism may comprise a step of introducing a mutation for expressing a polypeptide having 3-methyl-2-oxobutanoate hydroxymethyltransferase activity into the microorganism.

The step of introducing the mutation may comprise a step of introducing (transforming) a polynucleotide encoding the polypeptide having 3-methyl-2-oxobutanoate hydroxymethyltransferase activity or a recombinant vector comprising the polynucleotide, into the microorganism.

Another embodiment provides a method of producing a pantothenic acid and/or pantoic acid, the method comprising a step of culturing a microorganism having an enhanced3-methyl-2-oxobutanoate hydroxymethyltransferase activity as described above, in a medium. The method may further comprising, after the step of culturing, recovering the pantothenic acid or pantoic acid from the cultured microorganism, the medium, or both of them.

In the method, the step of culturing the microorganism may be performed by known batch culturing methods, continuous culturing methods, fed-batch culturing methods, etc., but with no particular limitation thereto. Here, culture conditions may be maintained at an optimal pH (e.g., a pH of 5 to 9, specifically a pH of 6 to 8, and most specifically a pH of 6.8) using a basic compound (e.g., sodium hydroxide, potassium hydroxide, or ammonia) or an acidic compound (e.g., phosphoric acid or sulfuric acid), or at an aerobic condition by supplying oxygen or oxygen-containing gas mixture to a cell culture, but with no particular limitations thereto. The culture temperature may be maintained at 20 to 45° C. or specifically at 25 to 40° C., and the cells may be cultured for about 10 to 160 hours, but with no limitations thereto. The pantothenic acid and/or pantoic acid produced by the culturing may be exported to the culture medium or remain within the cells.

A medium available for the culturing may comprise, but not be limited to, at least one selected from the group consisting of sugar and carbohydrate (e.g., glucose, sucrose, lactose, fructose, maltose, molasses, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid), as a carbon source, respectively or in combination. As a nitrogen source, at least one selected from the group consisting of nitrogen-containing organic compounds (e.g., peptone, yeast extract, meat juice, malt extract, corn solution, soybean meal powder, and urea), inorganic compounds (e.g., ammonium sulfate, ammonium chloride, ammonium phosphate, ammonium carbonate, and ammonium nitrate), and the like, may be comprised respectively or in combination, without being limited thereto. As a phosphorus source, at least one selected from the group consisting of potassium dihydrogen phosphate, dipotassium phosphate, sodium-containing salt corresponding thereto, and the like, may be comprised respectively or in combination, without being limited thereto. In addition, the medium may comprise other essential growth-stimulating substances, such as metal salts (e.g., magnesium sulfate or ferrous sulfate), amino acids, and/or vitamins.

In the step of recovering the pantothenic acid and/or pantoic acid, the pantothenic acid and/or pantoic acid of interest may be collected from the medium, the culture solution, or the microorganisms, using a suitable method known in the art according to the culturing method. By way of example, the recovering step may be carried out using at least one method selected from centrifugation, filtration, anion exchange chromatography, crystallization, HPLC, and the like. The method of producing pantothenic acid and/or pantoic acid may further comprise a purification step, prior to, simultaneously with, or subsequent to the recovering step.

Advantageous Effects

The present disclosure provides a technology for increasing a pantothenic acid and/or pantoic acid production ability of a microorganism. For this purpose, *E. coli*-derived 3-methyl-2-oxobutanoate hydroxymethyltransferase or variants thereof is provided. Introduction of a mutation for expressing the *E. coli*-derived 3-methyl-2-oxobutanoate hydroxymethyltransferase or a variant thereof into a microorganism may result in improving a pantothenic acid and/or pantoic acid production ability of the microorganism, or conferring a pantothenic acid and/or pantoic acid production ability to the microorganism.

MODE FOR INVENTION

Hereinafter, the present disclosure will be described in more detail with examples, but these examples are only for illustrative purpose and are not intended to limit the scope of the disclosure. It is clear to a person skilled in the art that the examples described below may be modified without departing from the spirit of the disclosure.

Example 1) Screening and Selecion of 3-Methyl-2-Oxobutanoate Hydroxymethyltransferase Genes As a result of conducting NCBI BLAST searching using the 3-methyl-2-oxobutanoate hydroxymethyltransferase coding gene (panB) of *Corynebacterium glutamicum* ATCC13032 as a query, candidate genes, which are estimated as having a 3-methyl-2-oxobutanoate hydroxymethyltransferase coding gene activity, and microorganisms comprising the candidate gene were selected. Among the microorganisms, 3-methyl-2-oxobutanoate hydroxymethyltransferase coding genes, which are derived from microorganisms having biosafety level 1 among the microorganisms, were selected and summarized in Table 1:

TABLE 1

| Microorganisms expected as comprising 3-methyl-2-oxobutanoate hydroxymethyltransferase coding gene and primers/plasmids used in selecting the 3-methyl-2-oxobutanoate hydroxymethyltransferase genes | | | | |
|---|---|---|---|---|
| | Microorganism name | KCTC Accession No. | primers | plasmid |
| 1 | *Escherichia coli* | ATCC47076 | SEQ ID NO: 1, 2 | pECCG117-panB(EC) |
| 2 | *Bacillus subtilis* | KCTC3135(ATCC 6051) | SEQ ID NO: 3, 4 | pECCG117-panB(BS) |
| 3 | *Pantoea agglomerans* | KCTC2564(ATCC27155) | SEQ ID NO: 5, 6 | pECCG117-panB(PA) |
| 4 | *Serratia rubidaea* | KCTC2927(ATCC27593) | SEQ ID NO: 7, 8 | pECCG117-panB(SR) |
| 5 | *Serratia proteamaculans* | KCTC2936(ATCC19323) | SEQ ID NO: 9, 10 | pECCG117-panB(SP) |
| 6 | *Pseudomonas resinovorans* | KCTC12498(ATCC14235) | SEQ ID NO: 11, 12 | pECCG117-panB(PR) |
| 7 | *Pedobacter terrae* | KCTC12762(DSM17933) | SEQ ID NO: 13, 14 | pECCG117-panB(PT) |
| 8 | *Citrobacter bitternis* | KCTC42139(JCM30009) | SEQ ID NO: 15, 16 | pECCG117-panB(CB) |
| 9 | *Enterobacter cloacae* | KCTC2519(ATCC23355) | SEQ ID NO: 17, 18 | pECCG117-panB(ECI) |
| 10 | *Achromobacter piechaudii* | KCTC22890(ATCC43552) | SEQ ID NO: 19, 20 | pECCG117-panB(AP) |
| 11 | *Staphylococcus epidermidis* | KCTC1917(ATCC12228) | SEQ ID NO: 21, 22 | pECCG117-panB(SE) |
| 12 | *Shigella flexneri* | KCTC12073 | SEQ ID NO: 23, 24 | pECCG117-panB(SF) |
| 13 | *Corynebacterium glutamicum* | KCTC9097(ATCC13032) | SEQ ID NO: 25, 26 | pECCG117-panB(CG) |

Example 2) Preparation of Microorganism Belonging to Genus *Corynebacterium* to which Foreign Microorganism Derived 3-Methyl-2-Oxobutanoate Hydroxymethyltransferase is Introduced After extracting genomes from the microorganisms obtained in Example 1, a PCR was performed using the genomes as templates and using the primers of Table 1, to amplify DNA fragments encoding 3-methyl-2-oxobutanoate hydroxymethyltransferase. The PCR was conducted using PfuUltra™ high-fidelity DNA polymerase (Stratagene), by repeating 30 cycles of denaturing at 95° C. for 30 seconds; annealing at 55° C. for 30 seconds, and polymerizing at 72° C. for 1 minute. As the results, each 3-methyl-2-oxobutanoate hydroxymethyltransferase coding DNA fragment (panB) was obtained.

To prepare *Corynebacterium glutamicum* derived PLM1 promoter, a PCR was performed using the genome DNA of *Corynebacterium glutamicum* (ATCC13032) as a template and using primers of SEQ ID NOS: 27 and 28 under the above conditions, to obtain the promoter DNA fragment.

pECCG117 vector (Korean Patent No. 10-0057684), which was treated with restriction enzyme BamHI followed by heat treatment at 65° C. for 20 minutes, and the above obtained DNA fragments (each panB, PLM1 promoter) were mixed in a ratio of 2:1:1 (pECCG117 vector:panB:PLM1) based on a molar concentration (M), and cloned using Infusion Cloning Kit (TaKaRa) according to manufacturer's manual, to obtain plasmids. Names of the obtained plasmids and gene information which was introduced thereto were summarized in Table 1.

The 13 obtained vectors were transformed into *Corynebacterium glutamicum* ATCC 13032 by electroporation, thereby preparing strains expressing exogenous PanB (3-methyl-2-oxobutanoate hydroxymethyltransferase).

Example 3) Examination of Pantothenic Acid Production Ability of Foreign Microorganism-Derived 3-Methyl-2-Oxobutanoate Hydroxymethyltransferase Expressing Microorganism Belonging to Genus *Corynebacterium*

In order to examine pantothenic acid productivity of the strains expressing various foreign microorganism-derived panB prepared in Example 2, the strains and a parent strain (non-transformed strain) were respectively inoculated into a 250 ml corner-baffle flask containing 25 ml of a production medium, and then, cultured at 32° C. for 48 hours with shaking at 200 rpm, to produce pantothenic acid.

<Production Medium> glucose 10%, beta-alanine 0.5%, yeast extract 0.4%, ammonium sulfate 1.5%, monopotassium phosphate 0.1%, magnesium sulfate heptahydrate 0.05%, ferrous sulfate heptahydrate 10 mg/L, manganese sulfate monohydrate 6.7 mg/L, biotin 50 μg/L, thiamine.HCl 100 μg/L, pH 7.2

The obtained culture solution was centrifuged at 20,000rcf for 10 minutes, and then, the supernatant liquid was diluted to 1/10with TDW (triple distilled water) and subjected to HPLC analysis to measure the concentrations of pantothenic acid and L-valine. The obtained results are shown in Table 2 below.

TABLE 2

| | pantothenic acid concentration (g/L) | L-valine concentration (g/L) |
|---|---|---|
| ATCC13032 (wild-type) | 0.0 | 2.4 |
| ATCC13032 pECCG117-panB(EC) | 1.2 | 1.5 |
| ATCC13032 pECCG117-panB(BS) | 0.5 | 1.9 |
| ATCC13032 pECCG117-panB(PA) | 0.6 | 2.0 |
| ATCC13032 pECCG117-panB(SR) | 0.7 | 1.8 |
| ATCC13032 pECCG117-panB(SP) | 0.3 | 2.2 |
| ATCC13032 pECCG117-panB(PR) | 0.7 | 1.9 |
| ATCC13032 pECCG117-panB(PT) | 0.7 | 2.0 |
| ATCC13032 pECCG117-panB(CB) | 0.7 | 2.0 |
| ATCC13032 pECCG117-panB(ECI) | 0.6 | 2.1 |
| ATCC13032 pECCG117-panB(AP) | 0.6 | 1.9 |
| ATCC13032 pECCG117-panB(SE) | 0.5 | 2.0 |
| ATCC13032 pECCG117-panB(SF) | 0.7 | 1.9 |
| ATCC13032 pECCG117-panB(CG) | 0.6 | 2.0 |

As shown in Table 2, the parent strain, *Corynebacterium glutamicum* ATCC 13032, does not produce pantothenic acid, whereas all the tested foreign microorganism-derived panB expressing *Corynebacterium glutamicum* strains produced pantothenic acid of about 0.6 g/L in average. In particular, among the foreign microorganism-derived panB expressing strains, foreign *E. coli*-derived PanB expressing strain, ATCC13032 pECCG117-panB(EC), exhibited the highest pantothenic acid productivity (1.2 g/L).

The above results show that all 13 microorganism-derived enzymes (3-methyl-2-oxobutanoate hydroxymethyltransferases) selected in Example 1 exhibit pantothenic acid production ability, and among them, *E. coli*-derived enzyme hasspecially high pantothenic acid production ability.

Example 4) Preparation of Microorganism Belonging to Genus *Corynebacterium* to which *E. coli*-Derived 3-Methyl-2-Oxobutanoate Hydroxymethyltransferase Gene is Introduced A plasmid was prepared for introducing an *E. coli*-derived 3-methyl-2-oxobutanoate hydroxymethyltransferase coding gene (panB), which was evidenced as having excellent pantothenic acid production ability in Example 3, into *Corynebacterium glutamicum* ATCC13032.

First, a vector for deleting panB present in the parent strain (wild-type) was constructed. A PCR was performed using the genome DNA of *Corynebacterium glutamicum* ATCC13032 as a template and using the primers of SEQ ID NOS: 29 and 30, and SEQ ID NOS: 31 and 32. The PCR was performed by repeating 25 cycles of denaturing at 95° C. for 30 seconds; annealing at 55° C. for 30 seconds; and polymerization at 72° C. for 1 minute. As a result, a gene fragment of 1000 bp at upstream region of the panB gene and a gene fragment of 1000 bp at downstream region of the panB gene were obtained, respectively. Each amplification product was purified using QIAGEN's PCR purification kit and used as an insert DNA fragment for vector construction.

pDZ vector (U.S. Pat. No. 9,109,242 B2), which was treated with restriction enzyme smaI followed by heat treatment at 65° C. for 20 minutes, and the DNA fragments (the gene fragment of 1000 bp at upstream region of the panB gene and a gene fragment of 1000 bp at downstream region of the panB gene panB) were mixed in a ratio of 2:1:1 based on a molar concentration (M), and cloned using Infusion Cloning Kit (TaKaRa) according to manufacturer's manual, to construct pDZ_ΔpanB vector for deleting the panB gene from the chromosome.

To provide an *E. coli*-derived panB gene, a PCR was performed using plasmid pECCG117-panB(EC) prepared in Example 2 as a template and using primers of SEQ ID NOS: 33 and 34. The PCR was performed by repeating 25 cycles of denaturing at 95° C. for 30 seconds; annealing at 55° C. for 30 seconds; and polymerization at 72° C. for 1 minute. As a result, a DNA fragment of 1077 bp was obtained. The pDZ_ΔpanB vector, which was treated with restriction enzyme smaI followed by heat treatment at 65° C. for 20 minutes, and the above obtained DNA fragment, were mixed in a ratio of 1:2 based on a molar concentration (M), and cloned using Infusion Cloning Kit (TaKaRa) according to manufacturer's manual, to construct pDZ_ΔpanB::PLM1-panB(EC) vector for introducing the *E. coli*-derived panB gene into the chromosome.

*Corynebacterium glutamicum* ATCC 13032 was transformed with each of the constructed vectors pDZ_ΔpanB and pDZ_ΔpanB::panB(EC), and then subjected to a secondary crossover, thereby preparing a strain (ΔpanB strain) in which panB was deleted from its chromosome and a strain (ΔpanB::panB(EC) strain) in which panB was deleted from its chromosome and the *E. coli*-derived panB gene was introduced into the chromosome, respectively. A proper substitution with *E. coli*-derived panB gene was confirmed by MASA (Mutant Allele Specific Amplification) PCR method (Takeda et al., Hum. Mutation, 2, 112-117 (1993)) using primer combinations as below. Than is, a first determination was made by selecting strains that were amplified using a primer combination suitable for *E. coli*, SEQ ID NOS: 35 and 28, and SEQ ID NOS: 36 and 1, and then, a second conformation was made by analyzing the sequence of panB gene of the selected strains using a primer combination of SEQ ID NO: 35 and SEQ ID NO: 36.

To examine pantothenic acid production abilities of the above obtained mutants, *Corynebacterium glutamicum* ATCC 13032 wild-type strains, ΔpanB strains, and ΔpanB::panB(EC) mutants were respectively inoculated into 250 ml corner-baffle flask containing 25 ml of a production medium (referring to Example 3), and then, cultured at 32° C. for 48 hours with shaking at 200 rpm, to produce pantothenic acid.

The obtained culture solution was centrifuged at 20,000rcf for 10 minutes, and then, the supernatant liquid was diluted to 1/10with TDW (triple distilled water) and subjected to HPLC analysis to measure the concentrations of pantothenic acid and L-valine. The obtained results are shown in Table 3 below.

TABLE 3

| | pantothenic acid concentration (g/L) | L-valine concentration (g/L) |
|---|---|---|
| ATCC13032 (wild-type) | 0.1 | 1.9 |
| ATCC13032 ΔpanB | 0.0 | 2.7 |
| ATCC13032 ΔpanB ::panB(EC) | 0.4 | 1.3 |

As shown in Table 3, wild-type *Corynebacterium glutamicum* ATCC 13032 and the panB deleted (ΔpanB) strain displayed no or very poor production of pantothenic acid, whereas the foreign panB-expressing mutant *Corynebacterium glutamicum* (ΔpanB::panB(EC) strain) produced pantothenic acid at the concentration of 0.4 g/L.

Example 5) Preparation of Randomly Mutated Strains by Artificial Mutation (NTG-Based Mutation) and Selection of panB-Producing Strains In this example, in order to obtain microorganism mutants with more enhanced pantothenic acid production ability, a mutation of microorganism was induced as follows.

More specifically, *Corynebacterium glutamicum* ATCC ΔpanB::panB(EC) strains were activated by being cultured in an activation medium for 16 hours, inoculated on a seed medium sterilized at 121° C. for 15 minutes and cultured for 14 hours, and then, 5 ml of the obtained culture solution was collected. The collected culture solution was washed with 100 mM citric acid buffer, NTG (N-Methyl-N'-nitro-N-nitrosoguanidine) was added thereto so that its final concentration reaches to 200 mg/L and left for 20 minutes, and then, the resulted product was washed with 100 mM phosphate buffer. The NTG-treated strains were smeared on minimal medium, and their death rate was measured as 85%. The survived cells were inoculated and cultured on a production medium, and finally, a mutant exhibiting excellent pantothenic acid productivity were selected and named as *Corynebacterium glutamicum* CJVBS-01.

The compositions of the media used in this example were as follows:

<Activation Medium> beef extract 1%, polypeptone 1%, sodium chloride 0.5%, yeast extract 1%, agar 2%, pH 7.2

<Seed Medium> glucose 5%, Bacto peptone 1%, sodium chloride 0.25%, yeast extract 1%, urea 0.4%, pH 7.2

<Production Medium> glucose 10%, beta-alanine 0.5%, yeast extract 0.4%, ammonium sulfate 1.5%, monopotassium phosphate 0.1%, magnesium sulfate heptahydrate 0.05%, ferrous sulfate heptahydrate 10 mg/L, manganese sulfate monohydrate 6.7 mg/L, biotin 50 μg/L, thiamine.HC1100 μg/L, pH 7.2

<Minimal Medium> glucose 1.0%, ammonium sulfate 0.4%, magnesium sulfate 0.04%, monopotassium phosphate 0.1%, urea 0.1%, thiamine 0.001%, biotin 200 μg/L, agar 2%, pH 7.2

To examine pantothenic acid production ability of the above obtained mutant *Corynebacterium glutamicum* CJVB5-01, *Corynebacterium glutamicum* ΔpanB strain, ΔpanB::panB(EC) strain, and CJVB5-01 mutant were respectively inoculated into 250 ml corner-baffle flask containing 25 ml of a production medium, and then, cultured at 32° C. for 48 hours with shaking at 200 rpm, to produce pantothenic acid.

The obtained culture solution was centrifuged at 20,000rcf for 10 minutes, and then, the supernatant liquid was diluted to 1/10 with TDW (triple distilled water) and subjected to HPLC analysis to measure the concentrations of pantothenic acid and L-valine. The obtained results are shown in Table 4 below.

TABLE 4

Pantothenic acid productivity of NTG-based mutated strains

| | pantothenic acid concentration (g/L) | L-valine concentration (g/L) |
|---|---|---|
| ATCC13032 ΔpanB | 0.0 | 2.4 |
| ATCC13032 ΔpanB ::panB(EC) | 0.3 | 1.4 |
| CJVB5-01 | 1.2 | 1.0 |

As shown in Table 4, *Corynebacterium glutamicum* ΔpanB did not produce pantothenic acid, whereas foreign panB-inserted *Corynebacterium glutamicum* ΔpanB::panB (EC) strain produced pantothenic acid at the concentration of 0.3 g/L and the *Corynebacterium glutamicum* CJVB5-01 mutant produced pantothenic acid at the concentration of 1.2 g/L. From these results, it was confirmed that *Corynebacterium glutamicum* CJVB5-01 mutant displays more excellent pantothenic acid productivity.

From the genome sequencing result of the *Corynebacterium glutamicum* CJVB5-01 mutant, it was confirmed that the inserted *E. coli* panB gene is mutated, so as to encode a variant of wild-type *E. coli* 3-methyl-2-oxobutanoate hydroxymethyltransferase (SEQ ID NO: 37), to which G116A mutation (substitution of the amino acid corresponding to position 116 of the amino acid sequence of SEQ ID NO: 37, G(Gly), with A(Ala)) is introduced. Hereinafter, the indication of an amino acid mutation using amino acid position, such as 'G116A', may be understood to mean an amino acid mutation and/or a genetic mutation leading to such amino acid mutation.

The amino acid sequence of the *E. coli* 3-methyl-2-oxobutanoate hydroxymethyltransferase variant, to which G116A mutation is introduced, was indicated as SEQ ID NO: 62.

From the results, it was confirmed that the mutant obtained through the random mutagenesis method can produce pantothenic acid with high efficiency and high yield without inhibiting the pathway for pantothenic acid synthesis from pyruvic acid.

Example 6) Preparation of Mutant PanB Plasmid Having 3-Methyl-2-Oxobutanoate Hydroxymethyltransferase Activity In order to examine that the amino acid residue at position 116, which is a mutation position of the *E. coli* PanB (3-methyl-2-oxobutanoate hydroxymethyltransferase) and confirmed as affecting pantothenic acid productivity through Example 5, is important in increasing the pantothenic acid productivity, variants in which the position is substitution with various other amino acids were prepared and the effects thereof were examined. Using pECCG117-panB(EC) (referring to Table 1) prepared in Example 2 as a template and using primers of Table 5 below, 19 variants having a random mutation (saturated mutagenesis) in which the amino acid of position 116 of *E. coli* PanB (SEQ ID NO: 37), G(Gly), is substituted with other amino acid (that is, the variants are mutated by introducing mutated panB gene encoding the randomly mutated *E. coli* PanB) were prepared. The substituted amino acids of the variant mutated by each saturated mutagenesis and primers used therefor are summarized in Table 5 below.

TABLE 5

| Template | Amino acid substitution | Primers used |
|---|---|---|
| pECCG117-panB(EC) | G116S | SEQ ID NO: 27, 38/39, 28 |
| | G116C | SEQ ID NO: 27, 40/41, 28 |
| | G116L | SEQ ID NO: 27, 42/43, 28 |
| | G116I | SEQ ID NO: 27, 44/45, 28 |
| | G116T | SEQ ID NO: 27, 46/47, 28 |
| | G116V | SEQ ID NO: 27, 48/49, 28 |
| | G116M | SEQ ID NO: 27, 50/51, 28 |
| | G116D | SEQ ID NO: 27, 52/53, 28 |
| | G116E | SEQ ID NO: 27, 54/55, 28 |
| | G116N | SEQ ID NO: 27, 56/57, 28 |
| | G116Q | SEQ ID NO: 27, 58/59, 28 |
| | G116A | SEQ ID NO: 27, 60/61, 28 |

In particular, a PCR was performed using primers presented in Table 5 and using pECCG117-panB(EC) (Table 1) prepared in Example 2 as a template. As a polymerase, Solg™ Pfu-X DNA polymerase (SolGent co., Ltd.) was employed. The PCR was performed by repeating 25 cycles of denaturing at 95° C. for 10 minutes, followed by denaturing at 95° C. for 30 seconds, annealing at 55° C. for 30 seconds, and polymerizing at 72° C. for 1 minute. As a result, DNA fragments of 610 bp of 5' upstream region and 470 bp of 3' downstream region centering the mutation site of 3-methyl-2-oxobutanoate hydroxymethyltransferase gene were obtained.

pECCG117 vector (Korean Patent No. 10-0057684), which was treated with restriction enzyme BamHI followed by heat treatment at 65° C. for 20 minutes, and the above obtained DNA fragments (5' upstream 610 bp DNA fragment and 3' downstream 470 bp DNA fragment) were mixed in a ratio of 2:1:1 based on a molar concentration (M), and cloned using Infusion Cloning Kit (TaKaRa) according to manufacturer's manual, to obtain 19 mutant plasmids for introducing mutated panB. The information of the 19 mutant plasmids was summarized in Table 6.

TABLE 6

| Mutation position | Amino acid substitution | Mutant plasmid prepared for inducing the amino acid substitution |
|---|---|---|
| amino acid residue at position 116 of PanB (SEQ ID NO: 37) | G116S | pECCG117-panB(G116S) |
| | G116C | pECCG117-panB(G116C) |
| | G116L | pECCG117-panB(G116L) |
| | G116I | pECCG117-panB(G116I) |
| | G116T | pECCG117-panB(G116T) |
| | G116V | pECCG117-panB(G116V) |
| | G116M | pECCG117-panB(G116M) |
| | G116D | pECCG117-panB(G116D) |
| | G116E | pECCG117-panB(G116E) |

TABLE 6-continued

| Mutation position | Amino acid substitution | Mutant plasmid prepared for inducing the amino acid substitution |
|---|---|---|
| | G116N | pECCG117-panB(G116N) |
| | G116Q | pECCG117-panB(G116Q) |
| | G116A | pECCG117-panB(G116A) |

Example 7) Measurement of Pantothenic Acid Productivity of panB Variants Having Muta3-Methyl-2-Oxobutanoate Hydroxymethyltransferase Activity The mutant plasmid prepared in Example 6 and pECCG117-panB (WT-EC) (Table 1) were respectively introduced into the ATCC13032 ΔpanB strain prepared in Example 4 by electric pulse method, and then, smeared on a selective medium containing 25 mg/L of kanamycin, to obtain a total of 19 transformed mutant strains to which each random mutation (saturated mutagenesis) was introduced. Thereafter, a flask test was performed in the same manner as in Example 3, and pantothenic acid production abilities of the transformed mutant strains were measured. The results are shown in Table 7:

TABLE 7

| | pantothenic acid (g/L) | | | |
|---|---|---|---|---|
| Strain | Batch 1 | Batch 2 | Batch 3 | Average |
| ATCC 13032 ΔpanB (control) | 0.0 | 0.0 | 0.0 | 0.0 |
| ATCC 13032 ΔpanB pECCG117-panB(G116S) | 1.5 | 1.9 | 1.6 | 1.7 |
| ATCC 13032 ΔpanB pECCG117-panB(G116C) | 1.2 | 1.3 | 1.2 | 1.2 |
| ATCC 13032 ΔpanB pECCG117-panB(G116L) | 1.6 | 1.5 | 1.4 | 1.5 |
| ATCC 13032 ΔpanB pECCG117-panB(G116I) | 1.5 | 1.7 | 1.6 | 1.6 |
| ATCC 13032 ΔpanB pECCG117-panB(G116T) | 2.4 | 2.5 | 2.3 | 2.4 |
| ATCC 13032 ΔpanB pECCG117-panB(G116V) | 1.6 | 1.7 | 1.4 | 1.6 |
| ATCC 13032 ΔpanB pECCG117-panB(G116M) | 0.9 | 0.9 | 1.1 | 1.0 |
| ATCC 13032 ΔpanB pECCG117-panB(G116D) | 1.3 | 1.1 | 1.2 | 1.2 |
| ATCC 13032 ΔpanB pECCG117-panB(G116E) | 1.9 | 1.2 | 2.1 | 1.7 |
| ATCC 13032 ΔpanB pECCG117-panB(G116N) | 2.5 | 2.5 | 2.6 | 2.5 |

TABLE 7-continued

| | pantothenic acid (g/L) | | | |
|---|---|---|---|---|
| Strain | Batch 1 | Batch 2 | Batch 3 | Average |
| ATCC 13032 ΔpanB pECCG117-panB(G116Q) | 1.0 | 1.1 | 1.0 | 1.0 |
| ATCC 13032 ΔpanB pECCG117-panB(G116A) | 2.6 | 2.9 | 2.9 | 2.8 |
| ATCC 13032 ΔpanB pECCG117-panB(WT) | 0.9 | 0.8 | 1.0 | 0.9 |

As shown in Table 7, ATCC13032 ΔpanB strain did not produce pantothenic acid, whereas all the mutant strains to which *E. coli* PanB (wild-type) or a variant thereof is introduced displayed pantothenic acid production ability. In addition, the mutant strain to which mutation G116S, G116C, G116L, G1161, G116T, G116V, G116D, G116E, G116N, G116A, G116M, or G116Q is introduced produced pantothenic acid at higher level compared with ATCC 13032 ΔpanB pECCG117-panB(WT) which is a mutant strain having *E. coli* PanB (wild-type). As a result, it was confirmed that both wild-type and mutant forms of *E. coli* PanB exhibit the effect of increasing pantothenic acid production, in particular, the amino acid residue at position 116 of PanB (SEQ ID NO: 37) is an important position in pantothenic acid production, and when the amino acid at this position is substituted with various amino acids different from the original, the production ability of pantothenic acid was further increased.

ATCC 13032 ΔpanB pECCG117-panB(G116A) strain (called as *Corynebacterium glutamicum* CV03-5001), which is confirmed as having the most excellent pantothenic acid producing ability in this example, was deposited with the Korea Culture Center of Microorganisms located in Hongje-dong, Seodaemun-gu, Seoul, Korea, a depository institution under the Budapest Treaty, on Jun. 8, 2020, and given the accession number KCCM12744P.

From the above description, it will be understood by those skilled in the art that the present disclosure may be embodied in other specific forms without departing from the spirit or essential characteristics thereof. In this regard, it should be understood that the embodiments described above are illustrative in all aspects and not restrictive. The scope of the present application is to be interpreted as being within the scope of the present application, all changes or modifications derived from the meaning and scope of the appended Claim s and from their equivalents rather than the detailed description.

Depository institution: Korea Culture Center of Microorganisms
Accession number: KCCM12744P
Accession date: 20200608

The invention claimed is:

1. A polypeptide comprising an amino acid sequence having at least 90% identity to the amino acid sequence of SEQ ID NO: 37, wherein the amino acid corresponding to position 116 of the amino acid sequence of SEQ ID NO: 37 is substituted with alanine (A, Ala), asparagine (N, Asn), threonine (T, Thr), glutamic acid (E, Glu), serine (S, Ser), valine (V, Val), isoleucine (I, Ile), leucine (L, Leu), aspartic acid (D, Asp), or cysteine (C, Cys).

wherein the polypeptide has an activity of 3-methyl-2-oxobutanoate hydroxymethyltransferase.

2. The polypeptide of claim 1, wherein the amino acid corresponding to position 116 of the amino acid sequence of SEQ ID NO: 37 is substituted with alanine (A, Ala).

3. The polypeptide of claim 1, comprising the amino acid sequence selected from the group consisting of SEQ ID NO: 62 to SEQ ID NO: 71.

4. A polynucleotide encoding the polypeptide of claim 1.

5. A microorganism producing a pantothenic acid or pantoic acid, which comprises the polypeptide according to claim 1 or a polynucleotide encoding the polypeptide.

6. The microorganism of claim 5, wherein the microorganism belongs to the genus of *Corynebacterium* or *Escherichia.*

7. The microorganism of claim 6, wherein the microorganism belonging to the genus of *Corynebacterium* is *Corynebacterium glutamicum.*

8. A method of producing a pantothenic acid or pantoic acid, comprising:

culturing the microorganism of claim 5 in a medium.

9. The method of producing pantothenic acid or pantoic acid of claim 8, further comprising, after the step of culturing, recovering the pantothenic acid or pantoic acid from the cultured microorganism, the medium, or both of them.

* * * * *